United States Patent [19]

Darnell

[11] 4,430,991
[45] Feb. 14, 1984

[54] SURGICAL RETRACTOR STAY DEVICE AND TUBE CONNECTOR

[75] Inventor: W. Dale Darnell, Caledonia, Miss.

[73] Assignee: Humboldt Products Corp., Columbus, Miss.

[21] Appl. No.: 318,654

[22] Filed: Nov. 5, 1981

[51] Int. Cl.³ .............................................. A61B 17/02
[52] U.S. Cl. ...................................... 128/20; 128/341
[58] Field of Search ................. 128/20, 152, 341, 269, 128/343, 912, 345, 134; 285/239, 397; 24/208 A, 208 R

[56] References Cited

U.S. PATENT DOCUMENTS

| | | | |
|---|---|---|---|
| 1,042,624 | 10/1912 | Wagoner | 128/341 |
| 1,166,059 | 12/1915 | Ledbetter | 285/239 |
| 1,708,578 | 4/1929 | Hyde | 128/20 |
| 2,106,707 | 2/1938 | Greth | 128/341 |
| 2,630,805 | 3/1953 | Brehm | 128/341 |
| 2,714,269 | 8/1955 | Charles | 24/208 A |
| 3,799,100 | 3/1974 | Marriner | 24/208 R |
| 4,274,398 | 1/1981 | Scott | 128/20 |

FOREIGN PATENT DOCUMENTS

WO80/01460 7/1980 PCT Int'l Appl. ............... 128/343/

Primary Examiner—Edward M. Coven
Assistant Examiner—Max F. Hindenburg
Attorney, Agent, or Firm—Beveridge, DeGrandi & Kline

[57] ABSTRACT

A surgical retractor stay with a tissue holding hook affixed to the elastic hollow tubing member of the stay by a retaining member having a body in which the hook shank is embedded with the sharp end of the hook extending from one end of the body and a stud with a tapered knob on its outer end extending outwardly from the other end of the retaining member body, the size and configuration of the knob and stud being such as to be tightly retained within an end portion of the hollow tubing stretchingly installed thereover; and a surgical tube connector for joining a pair of hollow elastic surgical tube members having an elongated stud with tapered knobs at each end in which the stud and knobs are dimensioned for tight fitting containment within the end portions of the hollow tube members stretchingly installed thereover.

6 Claims, 5 Drawing Figures

SURGICAL RETRACTOR STAY DEVICE AND TUBE CONNECTOR

BACKGROUND OF THE INVENTION

This invention relates to surgical apparatus and particularly to an improvement in surgical retractors.

U.S. Pat. No. 4,274,398 discloses a surgical retractor comprising an annular frame conforming to the contour of the body portion on which surgery is to be performed and having a series of notches around the frame periphery into which are inserted elastic stay members that include lengths of elastic tubing to one end of some of which a tissue holding hook is attached. The tissue holding hooks of the stays have a looped handle which is retained within the tubing by inserting the handle into the tube while the tube is in a temporary malleable state, achievable by soaking one end of the tubing in a solvent. Installing the hook in a length of elastic tubing in the manner disclosed in the foresaid U.S. patent is tedious, time consumming and expensive and the stay configuration is limited to a single hook arrangement. At times different length stay members are needed for varying conditions encountered in the surgical operation and optimum lengths of elastic stay members and surgical tubes are not always available when needed. Although the stay members of the surgical retractor disclosed in U.S. Pat. No. 4,274,398 are satisfactory for many conditions, a greater versatility in the configuration of the stay tissue holding members of the retractor is needed.

SUMMARY OF THE INVENTION

An object of the invention is to provide an improved configuration of a tissue holding stay for a surgical retractor which can be quickly, easily and economically assembled.

Another object of the invention is to provide an easily assembled retractor tissue holding stay which has a high degree of security of attachment of the hook to the elastic member of the stay.

A further object of the invention is to provide a tissue holding retractor stay having multiple hooks arranged in various patterns and configurations.

Yet still another object of the invention is to provide a quickly attachable connector for joining together surgical retractory elastic stay members and surgical tubes in providing elastic stay members and surgical tubes of optimum lengths for all situations.

The foregoing and other similar objects are achieved by providing a surgical retractor stay in which the shank of a tissue holding hook is embedded in a retaining member body having an appended stud extending from the end of the body opposite the exposed hook and a tapered knob of larger dimensions than the stud on its outer end, the knob and stud being of a size and configuration to be frictionally retained within the end portion of the elastic tubing member of the stay stretchingly installed over and in tight engagement with the knob and stud. The objects are further achieved by providing a double knob connector generally similar in configuration to the tube retaining knob and stud arrangement of the above described retractor tissue holding stay but in which a tapered knob is incorporated on each end of a stud, whereby two stay members or hollow tubes can be joined by drawing the ends of the elastic hollow tube members of the respective stays or surgical tubes over the retaining knobs and around the adjacent areas of the stud of the connector.

DESCRIPTION OF PREFERRED EMBODIMENTS

All of the descriptive matter and drawings of U.S. Pat. No. 4,274,398 are incorporated in this application and reference thereto should be freely made in understanding the nature, use and arrangement of the present invention. It is to be understood that the stay members and connector of this invention are intended to be utilized in connection with surgical retractor frames of the nature disclosed in the aforesaid U.S. patent as replacements or adjuncts for the tissue supporting and holding stays of that patent.

Figure 2:
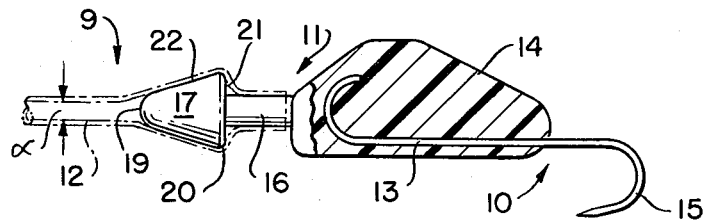
FIG. 2 is a side elevation partially in section of one end of a preferred embodiment of a tissue holding stay of the retractor of FIG. 1.

Reference should first be made to FIG. 2 which illustrates the tissue holding end of an improved stay 9 having a tissue holding hook 10 affixed by means of a retaining member 11 to the elastic member of the stay 9 comprising a length of hollow elastic tubing 12, which can conveniently be silicon rubber tubing. The shank portion 13 of the hook, of which an end portion may have a retaining curved portion, is embedded within the body 14 of the retaining member 11 with the hooked end 15 of the hook extending from the forward end of the body 14. A stud 16 integral with the body 14 extends from the end of the retaining member body opposite the outer end of the hook and the outer end of the stud has an integral tapered knob 17 forming a tapered enlargement on the stud outer end. Preferably the stud 16 is cylindrical with a substantially constant diameter greater than the internal diameter $a$ of the stay elastic tubing 12. A suitable stud diameter would be in the order of 1.5 times that of the tubing interior diameter and of a sufficient length to be contained within a substantial length of the elastic tubing of which a major portion is shown in phantom lines. The knob 17 is preferably a smoothly contoured body of revolution having a smoothly rounded front end surface 19 of relatively small radius for ease of insertion into the interior of the elastic tubing 12 and tapering outwardly from the front end to a maximum circumference at its rear end which forms the juncture 20 of the knob outer surface 22 with the knob rearwardly facing surface 21 which extends between the area of knob maximum diameter 20 and the stud 16 substantially perpendicular to the stud. However, it is visualized that for some applications the outwardly facing surfaces of the knob and the stud might be ridged or otherwise roughened to increase adherence to the tubing. The maximum circumferential dimension of the knob is substantially greater than that of the retaining member stud 16 and the external diameter of the elastic tubing 12 but within the range within which the elastic tubing is stretchable at normal room temperatures. The point of juncture 20 of the knob uppermost surface 22 at the point of maximum cross sectional area and the knob rearwardly facing surface 21 should be relatively sharp so as to establish an abrupt change of direction of the knob surface at the juncture point 20. This sharp corner and the respective diameters of the knob, stud and interior of the elastic tubing firmly retain the tubing on the retaining casing and resists separation of the tube from the casing from axially applied forces. The height dimension of the retaining member body 14 increases from the hook end toward the stud end to provide a substantial side surface area for ease of grasping by the surgeon in affixing and adjusting the stay in the retractor as described in the aforementioned patent. Conveniently the retaining member is a one piece molded plastic.

Figure 3:
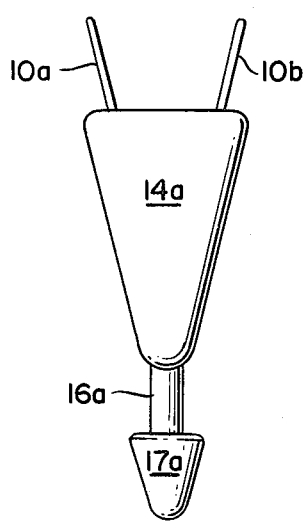
FIG. 3 is a plan view of another embodiment of an end portion of a tissue holding retractor having multiple hooks.

The width and depth of the body portions of the stay hook retaining member can be modified, as illustrated in FIG. 3, so as to accommodate two or more hooks 10a, 10b in providing a multi-hooked tissue holding stay. The several hooks 10a, 10b can be parallel or arranged in any other angular or spaced relationship as will provide better tissue holding and retaining provisions for particular applications. The contours of the body 14a of the multi-hooked retaining member need not be as illustrated and can be of any convenient shape as will accommodate the shank portions of the multiple hooks arranged in the desired pattern, the rear end portion of the body 14a having an appended stud 16a and tube retaining knob 17a of the same general configuration and relative sizes as discussed above with respect to the embodiment of FIG. 2.

Figure 4:
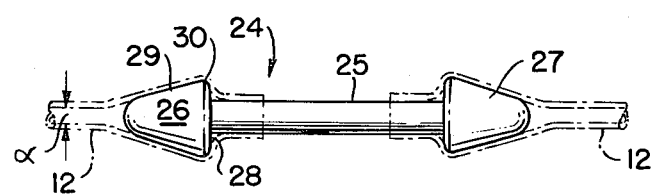
FIG. 4 is a side elevation of a surgical stay connector.
Figure 5:
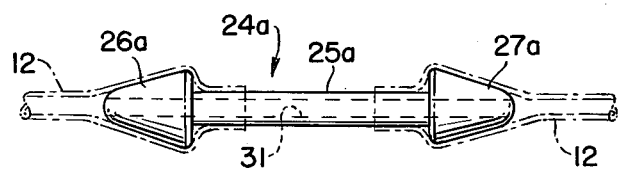
FIG. 5 is a side elevation of another embodiment of the connector shown in FIG. 4.

FIG. 4 illustrates a connector 24 that can be used to join together two lengths of elastic tubing (shown in phantom lines) of stay members for surgical retractor. Two or more lengths of elastic tubing are connectable by the connector 24 to form a continuous multi-segment elastic stay member of the nature of the one piece, long elastic stay members 25 or 26 that are illustrated in FIG. 5 of U.S. Pat. No. 4,274,398, which stay members extend from one side of the retractor frame to the other side under or around portions of the patient's anatomy involved in the surgery with both ends of the elastic stay members being retainingly inserted in appropriate notches in the retractor frame. Should it be necessary to increase the length of the elastic tubing member of a hook tissue holding stay of the nature disclosed in FIG. 2, the connector could be used to attach an additional length of elastic tubing to the end of the elastic tubing member of the tissue holding stay. The configuration of the connector illustrated in FIG. 4 is basically a double knob arrangement of the stud and knob end of a bodyless retaining member as described with respect to FIG. 2. The connector stud 25 of a diameter greater than the internal diameter α of the elastic tubing 12, shown in phantom lines in FIG. 4, has a pair of tapered knobs 26, 27 at each end, each knob having the same shape as that previously described for the retaining member of the stay described with respect to FIG. 2, i.e., preferably being a smoothly contoured body of revolution with a rounded front end tapering outwardly from the front end to the rearmost point of maximum circumferential dimension substantially greater than that of the stud 25 and having a sharp corner on the rear of the knob at the juncture of the knob rearwardly facing surface 28 with the knob outer surface 29 at the point of maximum circumference 30. Although it is contemplated that both ends of the connector would be symmetrical in order to join tubes of similar dimensions, the connector could be dimensioned to join tubes of different diameters. In this event, the portions of the stud adjacent each knob would have a different diameter that would accommodate the interior diameters of the different sized tubes and the dimensions of the respective knobs would have to be in proper proportion to the dimensions of the adjoining segments of the stud. Conveniently the connector 24 is a one piece molded plastic.

A further embodiment of a surgical tube connector 24a is illustrated in FIG. 5 in which the configuration is the same as in FIG. 4 but an axial passage 31 extends through the entire length of the connector comprising the stud 25a with the tapered knobs 26a and 27a at both ends. The purpose of the passage 31 is to allow air or other gases to flow freely through the hollow surgical tubes 12 that are joined by a connector 24a. By utilizing a connector of the nature illustrated in FIG. 5 lengths of hollow surgical tubes can be connected to form a continuous length through which a positive or negative pressure can be maintained. Obviously the hollow connector of FIG. 5 could be substituted for the solid connector of FIG. 4 in connecting lengths of surgical stay members as described in the preceding paragraph.

Figure 1:
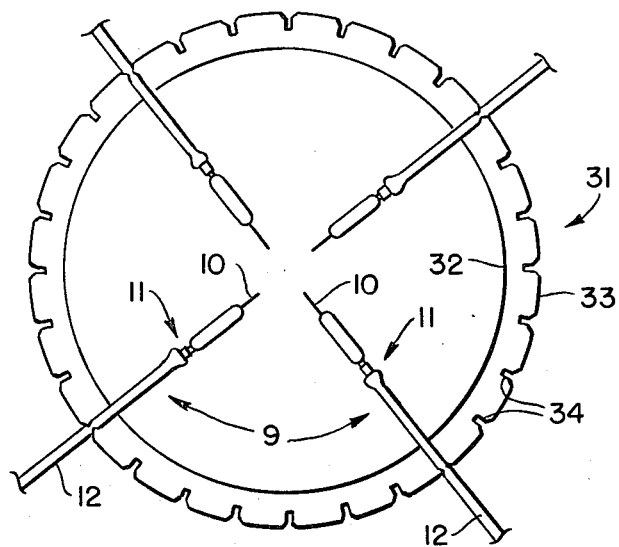
FIG. 1 is a plan view of a retractor showing tissue holding members in place.

For the convenience of anyone not having easy access to U.S. Pat. No. 4,274,398 incorporated herein, a simple representative surgical retractor with hook tissue holding stays is shown in FIG. 1 for illustrative and generally explanatory purposes. The retractor 31 has a generally annular frame 32 of rigid and easily sterilizable material, such as stainless steel, the frame being shaped to fit the surface contours of the body portion of the patient upon which surgery is to be performed. An outer, peripheral, upper lip 33 of the frame 31 contains a series of conveniently spaced-apart notches 34 into which the elastic tubing 12 of the stays 9 may be inserted and frictionally retained, the underside contours of the frame being such that a space exists between the lip 33 and the patient's body to permit access by the surgeon's fingers. The width of the notches 34 are less than the external diameter of the elastic tubing 12 of the stay and configured to retain the tubing without damage.

In utilizing the retractor, the frame 32 is placed in position to circumscribe the surface area of the body portion of the patient on which the operation is being performed. As incisions are made in the patient's body lying within the central open area of the frame 32, the surgeon utilizes the stays 9 to hold the wound open and can control the tension applied to the wound by inserting the elastic tubing member 12 of each stay in a notch 34 at a suitable point along the length of the elastic tubing 12. As the operation proceeds the surgeon can alter the shape and depth of the body tissue exposed by the incision opening by removing and reinserting the hook of a stay and by changing the position of stay elastic tubing member in the notches. FIG. 1 does not include an illustration of the patient's body and incision and the manner in which the retractor components are utilized in the operative procedure and reference should be made to U.S. Pat. No. 4,274,398 for a full understanding of the manner in which the improved stays and the connector of this invention are utilized in surgical operations.

It should be understood that the foregoing disclosure relates only to typical embodiments of the invention and that numerous modifications or alterations may be made therein without departing from the spirit and scope of the invention as set forth in the appended claims.

I claim:

1. A surgical retractor stay comprising:
   a retaining member having a body portion, an elongated stud portion extending from one end of said body portion, and an enlarged knob portion on the end of said elongated stud portion opposite said body portion;
   a hook member having a sharp hooked end and having a shank portion embedded within said retaining member body portion with said sharp hooked end protruding from the end thereof opposite said enlongated stud portion; and
   a length of hollow tubing having one end extending over said retaining member knob portion and at least a part of said retaining member stud portion;
   said retaining member knob portion and stud portion and the internal diameter of said hollow tubing being dimensioned for tight fitting containment and retention of said hollow tubing on said knob portion and stud portion when said hollow tubing is stretchingly installed thereover.

2. The stay of claim 1 wherein said knob portion tapers outwardly from a minimum dimension at the forward end thereof opposite the juncture of said knob portion with said stud portion to a rear end of maximum diameter substantially greater than that of said stud portion and wherein said stud portion has a greater diameter than the internal diameter of said hollow tubing.

3. The stay of claim 2 wherein the rearward most surface of said knob portion, extending between said stud portion and said knob portion maximum circumference, establishes an abrupt change of direction at its juncture with the knob portion surface forward of said knob portion maximum circumference.

4. The stay of claim 3 wherein said knob portion is a body of revolution having a smoothly rounded forward end tapering outwardly to said knob portion maximum circumference.

5. The stay of claims 2 or 3 wherein said retaining member knob portion, stud portion and body portion are an integral, solid mass.

6. A surgical retractor comprising a generally annular frame, contoured to the body portion on which surgery is to be performed with the frame having notches spaced apart around its periphery, and a plurality of stays, each of said stays including:
   a retaining member having a body portion, an elongated stud portion extending from one end of said body portion, and an enlarged knob portion on the end of said elongated stud portion opposite said body portion;
   a hook member having a sharp hooked end and having a shank portion embedded within said retaining member body portion with said sharp hooked end protruding from the end thereof opposite said enlongated stud portion; and
   a length of hollow tubing having one end extending over said retaining member knob portion and at least a part of said retaining member stud portion;
   said retaining member knob portion and stud portion and the internal diameter of said hollow tubing being dimensioned for tight fitting containment and retention of said hollow tubing on said knob portion and stud portion when said hollow tubing is stretchingly installed thereover;
   the notches of said frame and the external diameter of said tubing being dimensioned for frictional retention of said tubing within said notches when said tubing is inserted therein.

* * * * *